(12) United States Patent
Takeuchi et al.

(10) Patent No.: US 9,816,913 B2
(45) Date of Patent: *Nov. 14, 2017

(54) MICROPARTICLE MEASURING APPARATUS

(71) Applicant: SONY CORPORATION, Tokyo (JP)

(72) Inventors: Taichi Takeuchi, Kanagawa (JP); Shingo Imanishi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/231,146

(22) Filed: Aug. 8, 2016

(65) Prior Publication Data

US 2017/0030824 A1 Feb. 2, 2017

Related U.S. Application Data

(63) Continuation of application No. 14/434,404, filed as application No. PCT/JP2013/074002 on Aug. 30, 2013, now Pat. No. 9,429,508.

(30) Foreign Application Priority Data

Oct. 15, 2012 (JP) ................................. 2012-227954

(51) Int. Cl.
*G01N 15/02* (2006.01)
*G01N 15/14* (2006.01)
(Continued)

(52) U.S. Cl.
CPC ..... *G01N 15/1436* (2013.01); *G01N 15/1429* (2013.01); *G01N 15/1434* (2013.01);
(Continued)

(58) Field of Classification Search
CPC ........... G01N 15/1434; G01N 15/1459; G01N 15/05; G01N 15/1436; G01N 2015/1006; G01N 21/21; G01N 21/47; G01N 21/53
(Continued)

(56) References Cited

U.S. PATENT DOCUMENTS 6,266,302 B1 7/2001 Yamanaka
6,388,788 B1 * 5/2002 Harris ................ G02B 21/0028
250/234
(Continued)

FOREIGN PATENT DOCUMENTS

| JP | 61-025116 A | 2/1986 |
| JP | 09-166541 A | 6/1997 |
| JP | 2011-149822 A | 8/2011 |

*Primary Examiner* — Hoa Pham
(74) *Attorney, Agent, or Firm* — Chip Law Group (57) ABSTRACT

A microparticle measuring apparatus for highly accurately detecting the position of a microparticle flowing through a flow channel includes a light irradiation unit for irradiating a microparticle flowing through a flow channel with light, and a scattered light detection unit for detecting scattered light from the microparticle, including an objective lens for collecting light from the microparticle, a light splitting element for dividing the scattered light from the light collected by the objective lens, into first and second scattered light, a first scattered light detector for receiving an S-polarized light component, and an astigmatic element disposed between the light splitting element and the first scattered light detector, and making the first scattered light astigmatic. A relationship between a length L from a rear principal point of the objective lens to a front principal point of the astigmatic element, and a focal length f of the astigmatic element satisfies the following formula I.

$$1.5f \leq L \leq 2.5f \tag{I}$$

20 Claims, 9 Drawing Sheets

(51) Int. Cl.
*G01N 21/53* (2006.01)
*G01N 21/21* (2006.01)
*G01N 21/49* (2006.01)
*G01N 21/47* (2006.01)
*G01N 21/64* (2006.01)
G01N 15/10 (2006.01)
G01N 15/00 (2006.01)

(52) U.S. Cl.
CPC ......... *G01N 15/1459* (2013.01); *G01N 21/21* (2013.01); *G01N 21/47* (2013.01); *G01N 21/49* (2013.01); *G01N 21/53* (2013.01); *G01N 21/645* (2013.01); *G01N 2015/0065* (2013.01); *G01N 2015/1006* (2013.01); *G01N 2021/6478* (2013.01); *G01N 2201/0638* (2013.01); *G01N 2201/0683* (2013.01); *G01N 2201/06113* (2013.01)

(58) Field of Classification Search
USPC .......................................... 356/335–343, 73
See application file for complete search history.

(56) References Cited

U.S. PATENT DOCUMENTS

| 8,467,055 B2 | 6/2013 | Imanishi et al. |
| 9,429,508 B2* | 8/2016 | Takeuchi ........... G01N 15/1459 |
| 2005/0146718 A1 | 7/2005 | Bustamante et al. |
| 2009/0225305 A1* | 9/2009 | Hwang .............. G01B 11/0608 356/73 |
| 2015/0112627 A1 | 4/2015 | Nitta et al. |
| 2015/0177113 A1 | 6/2015 | Nitta |

* cited by examiner

L<1.5f, L>2.5f, Error-Signal=0

FIG. 7B

L<1.5f, L>2.5f, Error-Signal≠0

FIG. 7C 1.5f≤L≤2.5f, Error-Signal=0

MICROPARTICLE MEASURING APPARATUS

CROSS REFERENCE TO RELATED APPLICATIONS

The present application is a continuation of U.S. patent application Ser. No. 14/434,404 filed in USPTO on Apr. 8, 2015 which is a National Stage of PCT/JP2013/074002, filed Aug. 30, 2013, and claims the benefit of priority from Japanese Priority Patent Application JP 2012-227954 filed in the Japan Patent Office on Oct. 15, 2012. Each of the above referenced applications is hereby incorporated by reference in its entirety.

TECHNICAL FIELD

The present technique relates to a microparticle measuring apparatus for analyzing microparticles by an optical method. More specifically, the present technique relates to a microparticle measuring apparatus for detecting fluorescence or scattered light from the microparticles flowing through a flow channel by irradiating the microparticles with light.

BACKGROUND ART

An optical measurement method using flow cytometry (flow cytometer) is used for analysis of biological microparticles such as cells, microorganisms, or liposomes. The flow cytometer is an apparatus for irradiating the microparticles flowing through a flow channel formed in a flow cell, a microchip, or the like, with light, and detecting and analyzing fluorescence or scattered light emitted from each microparticle.

For example, for detection of fluorescence emitted from the microparticle, such as the cell or bead, using the flow cytometer, each microparticle is irradiated with light, as excitation light, having a specific wavelength at a predetermined intensity. After the fluorescence having been emitted from each microparticle is collected by a lens or the like, a filter, a dichroic mirror, or the like is employed to separate and select a target wavelengh, and the light is detected by a light receiving element such as a photomultiplier tube (PMT).

In the flow cytometer, a laminar flow is formed for passing the microparticles through substantially the center of the flow channel, but individual microparticles may have a variation in flowing position. Different flowing positions of respective microparticles bring about change in positional relationship between the microparticles and an optical system for light irradiation or light detection, detected intensity of the fluorescence or the scattered light is changed, and data accuracy is deteriorated. Therefore, a technique for detecting the flowing position of the microparticle for improving detection accuracy has been proposed (e.g., see Patent Documents 1 and 2).

In a fluid particle analyzing apparatus of Patent Document 1, detected light (scattered light) extracted from forward scattered light, sideward scattered light, or backward scattered light through a beam splitter, is detected by a quadrant photodiode, area charge coupled device (CCD), or the like. Misalignment between the center of excitation light and the center of a sheath flow is detected based on a detected position, and the position of a flow cell is adjusted so that the misalignment is within a predetermined range.

Further, Patent Document 2 discloses a technique for adjusting the focal position of excitation light or the position of a flow cell or a microchip by detecting positional information of a microparticle, using change in polarization angle generated in scattered light from the microparticle.

CITATION LIST

Patent Documents

Patent Document 1: Japanese Patent Application Laid-Open No. 9-166541
Patent Document 2: Japanese Patent Application Laid-Open No. 2011-149822

SUMMARY OF THE INVENTION

Problems to be Solved by the Invention

However, it cannot be said that the techniques of the above-mentioned Patent Documents 1 and 2 have sufficient accuracy to positionally detect the microparticles. Therefore, further improvement of detection accuracy has been demanded.

Therefore, it is an object of the present disclosure to provide a microparticle measuring apparatus for highly accurately detecting the position of a microparticle flowing through a flow channel.

Solutions to Problems

A microparticle measuring apparatus according to the present disclosure includes a light irradiation unit, and a scattered light detection unit. The light irradiation unit irradiates a microparticle flowing through a flow channel with light. The scattered light detection unit detects scattered light from the microparticle. The scattered light detection unit at least includes an objective lens, a light splitting element, a first scattered light detector, and an astigmatic element. The objective lens collects light emitted from the microparticle. The light splitting element divides the scattered light from the light having been collected by the objective lens, into first scattered light and second scattered light. The first scattered light detector receives the first scattered light. The astigmatic element disposed between the light splitting element and the first scattered light detector, and makes the first scattered light astigmatic. A relationship between a length L from a rear principal point of the objective lens to a front principal point of the astigmatic element, and a focal length f of the astigmatic element satisfies the following formula 1.

$$1.5f \leq L \leq 2.5f \qquad \text{[MATHEMATICAL FORMULA 1]}$$

Here, a "rear principal point" represents a principal point derived using parallel light input from the front side (light irradiation unit side) of an optical system, and light output from the rear side (detector side) of the optical system, and is also referred to as an image-side principal point. In addition, a "front principal point" represents a principal point derived using parallel light input from the rear side (detector side) of the optical system, and light output from the front side (light irradiation unit side) of the optical system, and is also referred to as an object-side principal point.

In the microparticle measuring apparatus, the light splitting element is a polarization element for diffracting the scattered light into an S-polarized light component and a P-polarized light component, and the first scattered light may be the S-polarized light component.

Further, for the astigmatic element, a cylindrical lens may be employed.

In this configuration, the astigmatic element can be disposed on a plane perpendicular to a y-direction to have an angle 0° to 5° between a generatrix of the astigmatic element and a line extending in an x-direction or a line extending in a z-direction, wherein a light input direction to the microparticle is defined as the z-direction, a flowing direction of the microparticle is defined as the x-direction, and a direction perpendicular to the z- and x-directions is defined as the y-direction.

The first scattered light detector may be a detector having a light receiving surface divided into a plurality of areas, and may employ, for example, a quadrant photodiode.

In this case, the first scattered light detector can be disposed on a plane perpendicular to the y-direction to have an angle of 40° to 50° between a dividing line of the first scattered light detector and a line extending in the x-direction or a line extending in the z-direction, wherein the light input direction to the microparticle is defined as the z-direction, the flowing direction of the microparticle is defined as the x-direction, and the direction perpendicular to the z- and x-directions is defined as the y-direction.

Further, in this microparticle measuring apparatus, a flowing position of the microparticle can be detected based on the change in light receiving position of the first scattered light.

When the light receiving surface of the first scattered light detector is divided into a lattice shape to have a first area, a second area, a third area, and a fourth area, the first scattered light detector can acquire the positional information of the microparticle based on a difference (A–C) between a detection value A of the first area and a detection value C of the third area not adjacent to the first area.

Alternatively, the positional information of the microparticle can be also acquired based on a difference ((A+C)–(B+D)) between the sum (A+C) of the detection value A of the first area and the detection value C of the third area not adjacent to the first area, and the sum (B+D) of a detection value B of the second area adjacent to the first area and a detection value D of the fourth area not adjacent to the second area.

Further, the light irradiation unit may irradiate the microparticle flowing through an analysis chip including a microchannel, with light.

Effects of the Invention

According to the present disclosure, since the influence of positional fluctuation of the microparticle in a flowing direction is restricted, the position of the microparticle flowing through the flow channel can be detected highly accurately, as compared with a conventional one.

MODE FOR CARRYING OUT THE INVENTION

A mode for carrying out the present disclosure will be described below in detail with reference to accompanying drawings. The present disclosure is not intended to be limited to each embodiment described below. Description will be made in the following order.

1. First Embodiment (an example of a generatrix of an astigmatic element arranged perpendicular to the x-axis)

2. Modification of First Embodiment (an example of the generatrix of the astigmatic element arranged parallel with the x-axis)

1. First Embodiment

As the results of intensive experiments and studies have been conducted in order to solve the problem described above, the present inventor has obtained the knowledge described below. In the above-mentioned techniques of Patent Documents 1 and 2, the scattered light emitted when the microparticle is irradiated with a laser beam is projected on a light receiving element. The scattered light projected on the light receiving element is sensitive to the position of a particle in an objective view, and when the position of the particle is changed, its projected position and shape on the light receiving element are changed.

The change in the projected position and shape is detected by the light receiving element to map a particle passage position in a flow channel. Further, various light detection values are corrected based on positional information of the microparticle, and therefore, improvement of a value of a coefficient of variation (CV) or improvement of accuracy in fluorescence spectrum shape can be expected in intensities of fluorescence and the scattered light.

On the other hand, in the techniques of Patent Documents 1 and 2, the positional information of the microparticle is obtained in two directions, i.e., a direction perpendicular to a microparticle flow and an optical axis direction of the excitation light, and fluctuation of the microparticle in the flowing direction is superposed as an error on these two kinds of positional information. At this time, in order to further accurately detect a flowing position of the microparticle, it is necessary to restrict the fluctuation of the microparticle in the flowing direction.

Therefore, in a microparticle measuring apparatus according to the present embodiment, in order to improve microparticle position detection accuracy, a position detecting optical system is arranged in a specific configuration to restrict the influence of positional fluctuation of the microparticle in a flowing direction.

[Overall Configuration of Apparatus]

Figure 1:
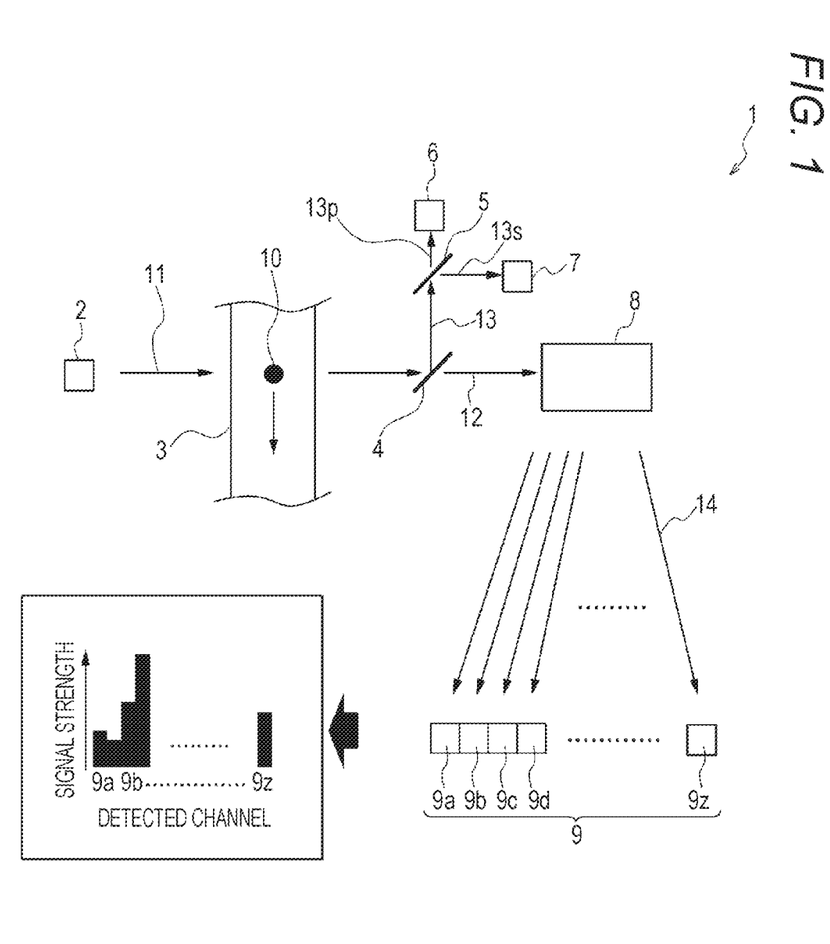
FIG. 1 is a schematic diagram illustrating a microparticle measuring apparatus according to a first embodiment of the present disclosure.

The microparticle measuring apparatus according to the present embodiment includes a light irradiation unit, and a light detection unit. The light irradiation unit irradiates a microparticle flowing through a flow channel with light. The light detection unit detects fluorescence or scattered light emitted from the microparticle. FIG. 1 is a schematic diagram illustrating the microparticle measuring apparatus according to the present embodiment.

[About Microparticle 10]

The microparticle 10 measured by the microparticle measuring apparatus 1 according to the present embodiment is preferably a microparticle emitting fluorescence 12 and scattered light 13 by being irradiated with excitation light 11, and includes a biological microparticle such as a cell, a microorganism, or a ribosome or a synthetic particle such as a latex particle, a gel particle, or an industrial particle.

The biological microparticles includes a chromosome, a ribosome, a mitochondrion, organelle, or the like constituting various cells. The cell includes a plant cell, an animal cell, a hematopoietic cell, or the like. Further, the microorganism includes a bacterium such as a colon bacillus, a virus such as tobacco mosaic virus, a fungi such as yeast, or the like. The biological microparticle may also include a biological polymer such as nucleic acid, protein, or a conjugate thereof.

On the other hand, an industrial particle includes, for example, an organic polymer material, an inorganic material, or a metal material. The organic polymer material may include a polystyrene, a styrene-divinylbenzene, a polymethyl methacrylate, or the like. In addition the inorganic material may include glass, silica, a magnetic material, or the like. The metal material may include, for example, a gold colloid or aluminum. These microparticles generally have a spherical shape, but may have a non-spherical shape, and are also not intended to be limited particularly in size or mass.

[Configuration of Light Irradiation Unit]

The light irradiation unit includes an objective lens configured to collect the excitation light 11 toward the microparticle 10, in addition to a light source 2 configured to emit the excitation light 11. The light source 2 used here can be selected appropriately according to measurements or the like, but for example a laser diode, second harmonic generation (SHG) laser, a gas laser, or a high brightness light emitting diode (LED) can be employed.

Further, a band-pass filter (not illustrated) can be also disposed between the light source 2 and the objective lens. The band-pass filter only passes light having a specific wavelength and reflects the other light. The light irradiation unit preferably has a configuration for irradiating the microparticle 10 with the light having a specific wavelength (excitation light 11), the kinds and arrangement of various optical components such as the light source, the lens, and an optical filter can be appropriately selected, and not intended to be limited to the above-mentioned configuration.

[Configuration of Light Detection Unit]

The light detection unit includes a fluorescence detection unit configured to detect the fluorescence 12, and a scattered light detection unit configured to detect the scattered light 13. The objective lens (not illustrated), a spectral filter 4, or the like are arranged between the fluorescence detection unit and the scattered light detection unit, and the microparticle 10. The objective lens collects the fluorescence 12 or the scattered light 13 emitted from the microparticle 10, and the spectral filter 4 separates the fluorescence 12 and the scattered light 13.

(Fluorescence Detection Unit)

The fluorescence detection unit is provided with a spectral element 8, a fluorescence detector 9, and the like. The spectral element 8 further separates the fluorescence 12 having been separated from the scattered light 13 into predetermined wavelengths, and the fluorescence detector 9 detects individual fluorescence 14 having been diffracted by the spectral element 8. As the fluorescence detector 9, for example, a light receiving element array having a plurality of independent detection channels arranged side by side. Specifically, a two-dimensional light receiving element such as a charge coupled device (CCD) or a complementary metal oxide semiconductor (CMOS) can be employed, in addition to a PMT array, a photodiode array, or the like in which light receiving elements $9a$ to $9z$, such as a photo-multiplier tube (PMT) or a photo diode (PD), are one-dimensionally arranged.

Additionally, in the microparticle measuring apparatus 1 according to the present embodiment, multiple combination of a wavelength selection element such as a filter or a dichroic mirror, and the light receiving element such as the PMT allows detection and analysis of a plurality of kinds of fluorescent pigments. Further, a plurality of excitation light sources having different wavelengths is combined to increase the number of analyzable colors.

(Scattered Light Detection Unit)

The scattered light detection unit is provided with a scattered light intensity detector 6 and a particle position detector 7, and a polarization element 5 or the like. The scattered light intensity detector 6 and the particle position detector 7 detect the scattered light 13 emitted from the microparticle 10, and the polarization element 5 or the like is served as a light splitting element configured to split the scattered light 13 into two components.

The polarization element 5 separates input non-polarized light into two polarized light components having vibration directions perpendicular to each other, and in the microparticle measuring apparatus 1 according to the present embodiment, scattered light 13 is separated into S-polarized light $13s$ and P-polarized light $13p$. Specifically, the polarization element 5 passes the P-polarized light $13p$ of the input scattered light 13, and reflects the S-polarized light $13s$. Therefore, only the P-polarized light $13p$ is input into the scattered light intensity detector 6, and only the S-polarized light $13s$ is input into the particle position detector 7.

Further, the scattered light intensity detector 6 detects the intensity of forward scattered light emitted from the microparticle 10, and preferably detects the P-polarized light 13p diffracted by the polarization element 5. As described above, the intensity of the forward scattered light (P-polarized light 13p) is detected, and thereby information about for example the size of the microparticle 10 can be obtained.

The particle position detector 7 detects the change in polarization angle of the scattered light 13 emitted from the microparticle 10, and preferably detects the S-polarized light 13s diffracted by the polarization element 5. The microparticle position detector 7 may employ a detector having a light receiving surface divided into a plurality of areas, especially, a quadrant photodiode, a CCD, or the like.

In the microparticle 10, a light scattering phenomenon of the excitation light 11 causes change in polarization angle between the excitation light 11 and the scattered light 13. For example, the position of the microparticle 10 in the flow channel 3 can be understood, when only the P-polarized light is polarized as the excitation light 11 emitted from the light source 2, only a component (S-polarized light 13s) having a rotated polarization angle is separated from the scattered light 13 generated in the microparticle 10, and detected by the particle position detector 7.

[About Position Detecting Optical System]

Figure 2:
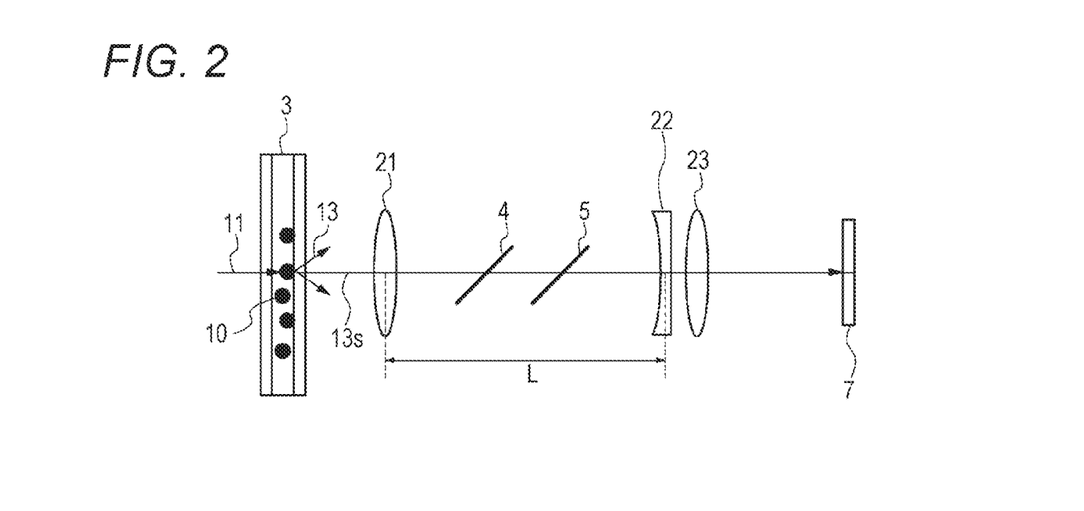
FIG. 2 is a diagram illustrating an exemplary configuration of a position detecting optical system of the microparticle measuring apparatus 1 illustrated in FIG. 1.
Figure 3:
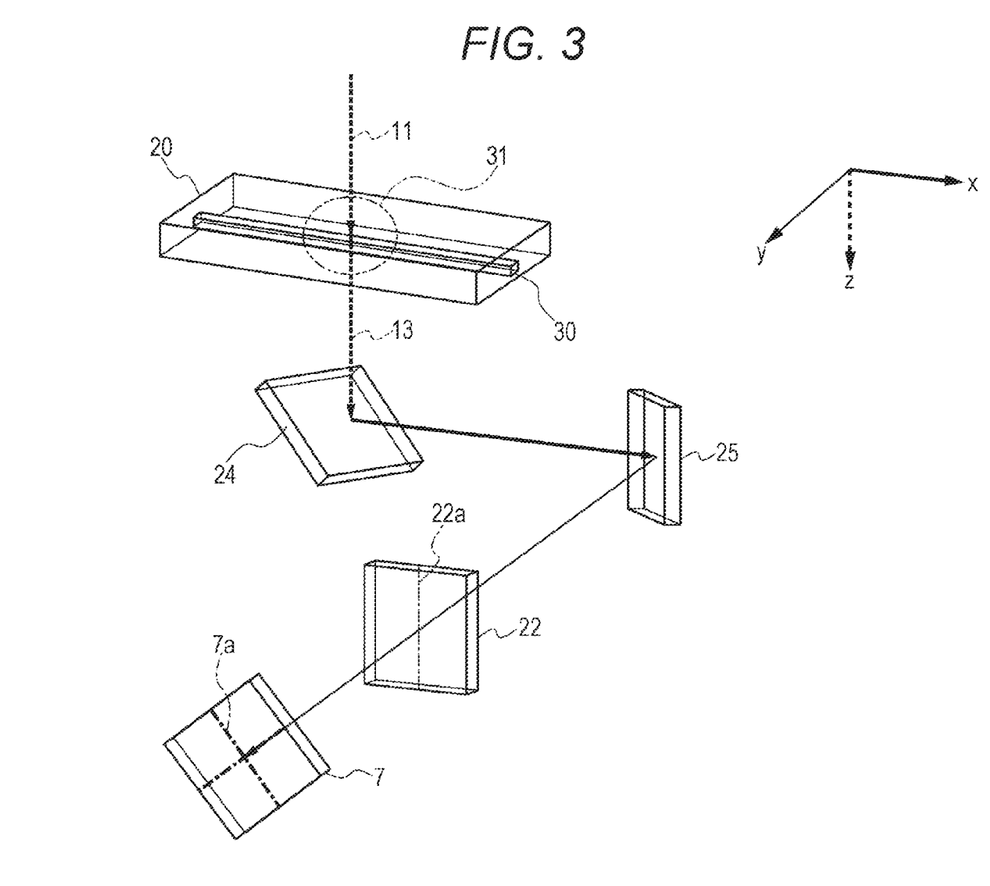
FIG. 3 is a schematic diagram illustrating arrangement of each optical component of the position detecting optical system illustrated in FIG. 2.

Next, a detailed description will be made of an optical system (position detecting optical system) configured to detect a flowing position of the microparticle 10 in the microparticle measuring apparatus according to the present embodiment 1. FIG. 2 is a diagram illustrating an exemplary configuration of the position detecting optical system of the microparticle measuring apparatus 1, and FIG. 3 is a schematic diagram illustrating arrangement of each optical component of the position detecting optical system. It is noted that, in FIGS. 1 to 3, components not particularly concerned with the explanation will be appropriately omitted for clarity of illustration.

As illustrated in FIG. 2, the position detecting optical system of the microparticle measuring apparatus 1 according to the present embodiment includes the objective lens 21, the spectral filter 4, the polarization element 5, an astigmatic element 22, a condensing lens 23, and the like. The objective lens 21 collects the scattered light 13 emitted from the microparticle 10, and the objective lens 21 preferably has a high numerical aperture NA, from a viewpoint of detection sensitivity.

The astigmatic element 22 intentionally makes a scattered light (S-polarized light 13s) flux astigmatic, and representatively includes a cylindrical lens. When the astigmatic element 22 is arranged in back of the condensing lens 23, a glass plate or the like arranged to be inclined to the traveling direction of the scattered light (S-polarized light 13s) can be also employed.

The condensing lens 23 is configured to collect the S-polarized light 13s made astigmatic by the astigmatic element 22 to the particle position detector 7. It is noted that the condensing lens 23 is not particularly limited in position, preferably arranged in front or back of the astigmatic element 22, and appropriately set according to its F number so that the S-polarized light 13s is collected on an image surface of the particle position detector 7.

The microparticle measuring apparatus 1 according to the present embodiment is designed so that a relationship between a length L from a rear principal point (image-side principal point) of the objective lens 21 to a front principal point (object-side principal point) of the astigmatic element 22 and a focal length f of the astigmatic element 22 satisfies the following formula 2. Here, the "rear principal point (image-side principal point)" represents a principal point derived using parallel light input from the front side (light irradiation unit side) of the optical system, and light output from the rear side (detector side) of the optical system. Further, the "front principal point (object-side principal point)" represents a principal point derived using parallel light input from the rear side (detector side) of the optical system, and light output from the front side (light irradiation unit side) of the optical system.

$$1.5f \leq L \leq 2.5f \qquad \text{[Mathematical Formula 2]}$$

Specifically, in the microparticle measuring apparatus 1 according to the present embodiment, the focal length f of the astigmatic element 22 is determined, or the positions of the objective lens 21 and the astigmatic element 22 are determined so as to satisfy the formula 2. It is noted that, when the relationship between the length L and the focal length f of the astigmatic element 22 does not satisfy the formula 2, signal fluctuation cannot be restricted upon occurrence of misalignment of the microparticle 10 in a flowing direction x. The relationship between the length L and the focal length f of the astigmatic element 22 is preferably expressed by L=2f, and therefore, an image can be formed at a constant position on the image surface regardless of the flowing position of the microparticle 10.

Whereas, as illustrated in FIG. 3, in the microparticle measuring apparatus 1 according to the present embodiment, the astigmatic element 22 preferably has a generatrix 22a arranged on the y-axis to be substantially perpendicular to the flowing direction x of the microparticle 10. Specifically, the astigmatic element 22 is preferably arranged on a plane perpendicular to the y-axis to have an angle of 0° to 5° between the generatrix 22a and a line extending in the z-axis direction.

Further, the particle position detector 7 is also arranged on the y-axis. For example, a quadrant detector preferably has a dividing line 7a arranged so as to be positioned substantially at ±45° to the flowing direction x of the microparticle 10. Specifically, the particle position detector 7 is preferably arranged on a plane perpendicular to the y-axis to have an angle of 40° to 50° between the dividing line 7a and a line extending in the x-axis direction and the z-axis direction. In this configuration, an angle between the generatrix 22a of the astigmatic element 22 and the dividing line 7a of the particle position detector 7 is also substantially ±45°.

Owing to such arrangement of the optical system, fluctuation of the microparticle in the flowing direction x is effectively restricted. It is noted that the term "fluctuation" represents change in height of an object represented by the scattered light 13, caused by change of the flowing position of the microparticle, and change in position and shape of the projected particle image on the particle position detector 7, brought about change in inclination of an optical axis.

In FIG. 3, a reference sign x indicates a direction in which a laminar flow 30 including the microparticles 10 flows in a microchip 20. A reference sign z indicates a radiation direction of the excitation light 11 irradiating an excitation light irradiation unit 31 of the microchip 20, and a reference sign y indicates a direction perpendicular to the x-direction and the z-direction. In FIG. 3, the x-direction and a y-direction are illustrated by solid lines, the z-direction is illustrated by a dotted line, and the same is applied to the traveling directions of the excitation light 11 and the scattered light 13. Further, when the optical system is arranged as illustrated in FIG. 3, the scattered light 13 is preferably adjusted in its traveling direction by mirrors 24 and 25 or the like.

[Operation]

Next, operation of the microparticle measuring apparatus 1, or a method for analyzing the microparticle 10 using the microparticle measuring apparatus 1 according to the present embodiment will be described. As illustrated in FIG. 1, in the microparticle measuring apparatus 1 according to the present embodiment, the excitation light 11 is radiated from the light source 2 provided at the light irradiation unit to the microparticle 10 flowing through the flow channel 3, and in the light detection unit, the fluorescence 12 or the scattered light 13 emitted from the microparticle 10 is detected.

Specifically, the fluorescence 12 emitted from the microparticle 10 is separated from the scattered light 13 by the spectral filter 4, is diffracted by the spectral element 8 such as a prism or a grating, and each diffracted fluorescence 14 is detected by each of the light receiving elements 9a to 9z of the fluorescence detector 9. In each of the light receiving elements 9a to 9z, an electric current or the like is electrically detected, and fluorescence intensity information is converted to electrical information. Based on the result, for example, a wavelength property of fluorescence intensity is analyzed and displayed. It is noted that, in the microparticle measuring apparatus 1 according to the present embodiment, a fluorescence spectrum can be also measured in addition to detection of a plurality of wavelength fragments with the filter.

Whereas, after the scattered light 13 emitted from the microparticle 10 is separated from the fluorescence 12 by the spectral filter 4, the scattered light 13 is diffracted into a P-polarized light component 13p and an S-polarized light component 13s by the polarization element 5. The P-polarized light component 13p is detected by the scattered light intensity detector 6, and the S-polarized light component 13s is detected by the particle position detector 7.

Figure 4:
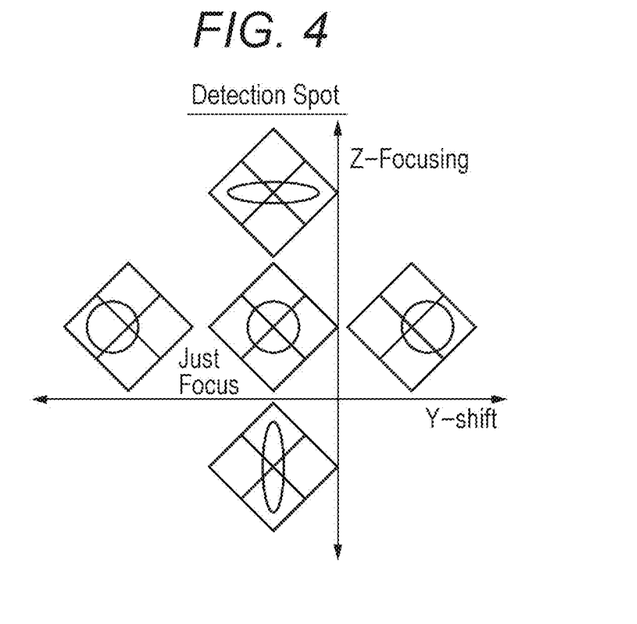
FIG. 4 is a diagram illustrating a relationship between flowing positions of microparticles 10 and projected images detected by a particle position detector 7.
Figure 5:
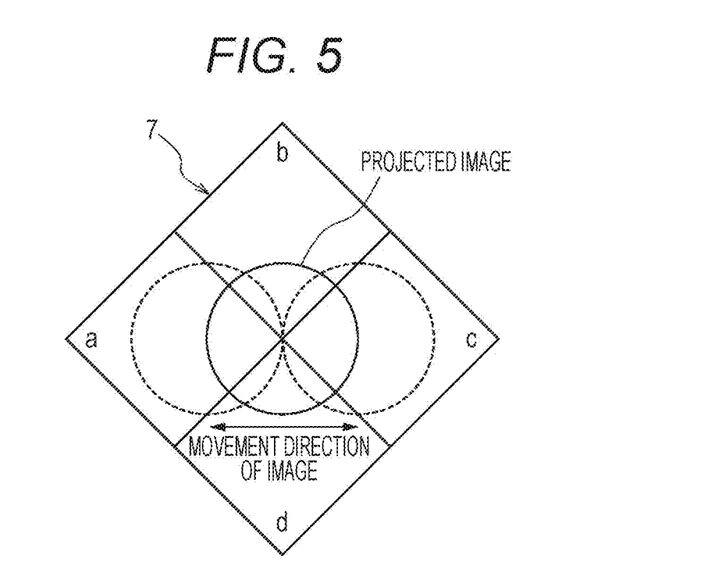
FIG. 5 is a diagram illustrating the movement of a projected image incidental to misalignment in a y-direction illustrated in FIG. 3.
Figure 6:
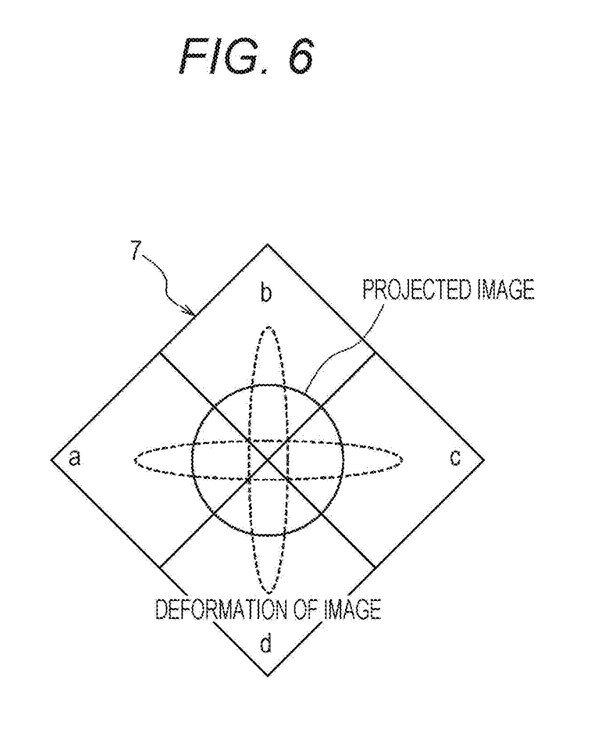
FIG. 6 is a diagram illustrating the movement of a projected image incidental to misalignment in a z-direction illustrated in FIG. 3.

FIG. 4 is a diagram illustrating a relationship between the flowing positions of the microparticles 10 and projected images detected by the particle position detector 7. FIG. 5 is a diagram illustrating the movement of a projected image incidental to misalignment in the y-direction illustrated in FIG. 3, and FIG. 6 is a diagram illustrating the movement of a projected image incidental to misalignment in the z-direction. Further, FIGS. 7A to 7C are diagrams illustrating the movement of projected images incidental to misalignment in the x-direction illustrated in FIG. 3.

The projected image obtained by the particle position detector 7 is an image formed by the S-polarized light 13s of the scattered light 13 emitted from the microparticle 10. As illustrated in FIG. 4, when the microparticle 10 exists at a focal position of the objective lens provided at the light irradiation unit, a full-circular image is provided, but when the microparticle exists at a position out of the focal position, an elliptical image is provided. The flowing position of the microparticle can be detected based on the change in light receiving position of the S-polarized light 13s.

For example, the particle position detector 7 is a quadrant detector, the misalignment of the microparticle 10 in the y-direction, illustrated in FIG. 5, can be calculated by (A-C), wherein signal values obtained in respective light receiving areas a, b, c, and d are defined as A, B, C, and D. Further, the misalignment of the microparticle 10 in the z-direction, illustrated in FIG. 6, is calculated by {(A+C)−(B+D)}.

Figures 7A, 7B:
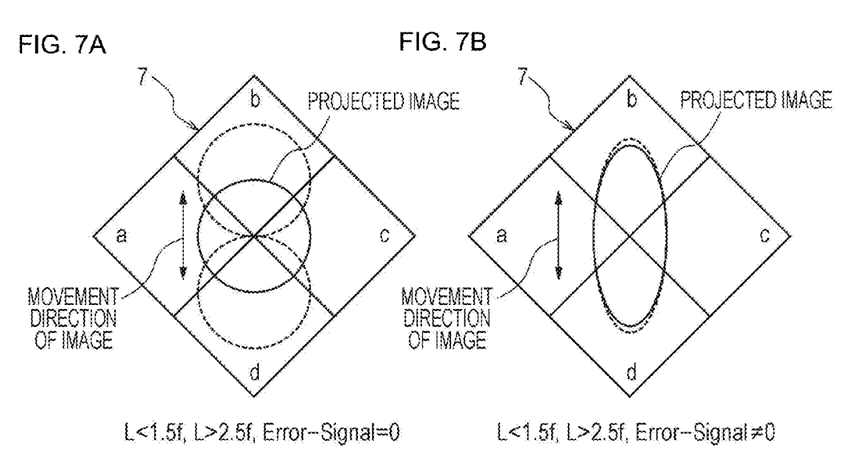
FIGS. 7A to 7C are diagrams illustrating the movement of projected images incidental to misalignment in an x-direction illustrated in FIG. 3.
Figure 7C:
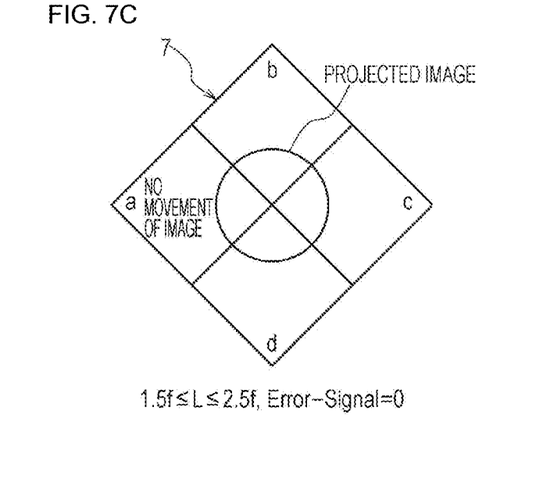

Whereas, as illustrated in FIG. 7A, the projected image of the particle position detector 7 is fluctuated also in a direction perpendicular to the movement caused by the misalignment of the microparticle 10 in the y-direction, illustrated in FIG. 5. A conventional detection method is configured such that, in such a condition, positional change of the projected image caused by fluctuation is superposed as an error upon calculation of the microparticle 10 in the y-direction and the z-direction, and this has been a cause of deterioration in detection accuracy. Further, offset of the position of the projected image from the center position of the particle position detector 7 reduces the effective diameter of the detector, and dynamic range of detection and linearity to a particle diameter are deteriorated.

The detector can be adjusted in position to restrict the fluctuation of the projected image caused by the misalignment, but in that case, as illustrated in FIG. 7B, the projected image is deformed into an elliptical shape, and therefore the dynamic range of detection and the linearity to the particle diameter is similarly deteriorated. In contrast, in the microparticle measuring apparatus according to the present embodiment, the optical system is arranged in a specific configuration, and therefore, fluctuation of the projected image caused by misalignment of the microparticle 10 in the flowing direction can be effectively restricted, as illustrated in FIG. 7C.

Figure 8A:
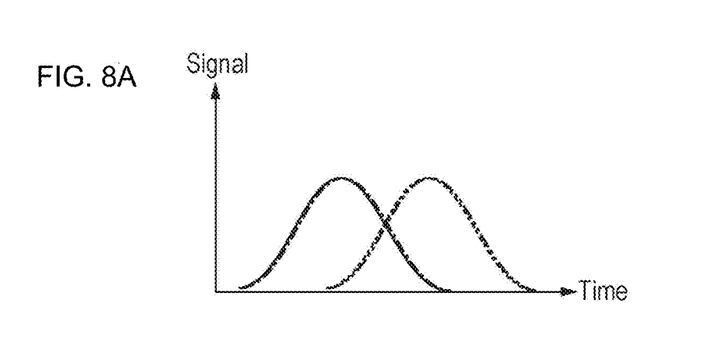
FIG. 8A is a diagram illustrating the behavior of a detection signal and FIG. 8B is a diagram illustrating the behavior of a projected image, when fluctuation of the microparticle in the flowing direction is not restricted.
Figure 8B:
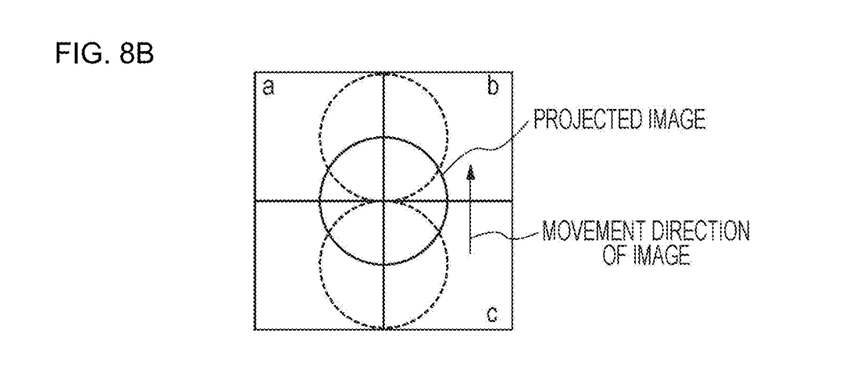
Figure 9A:
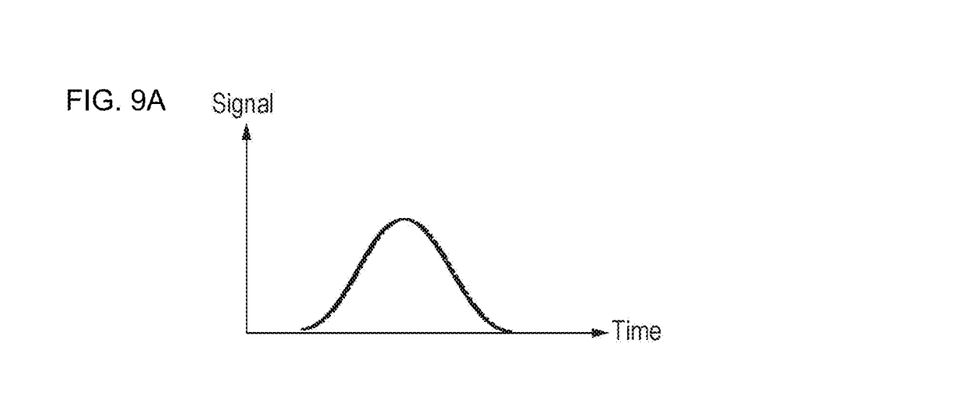
FIG. 9A is a diagram illustrating the behavior of a detection signal and FIG. 9B is a diagram illustrating the behavior of a projected image, when the fluctuation of the microparticle in the flowing direction is restricted.
Figure 9B:
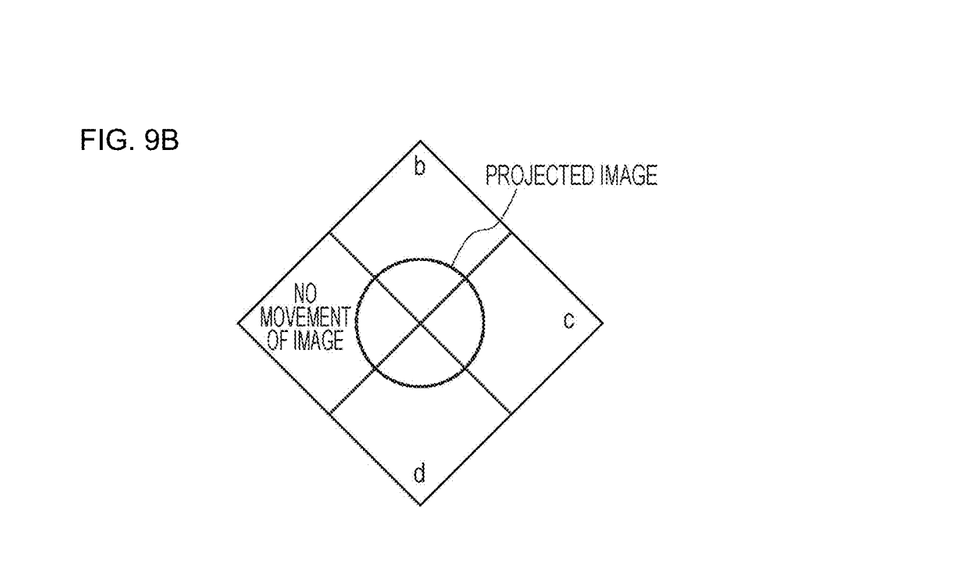

FIG. 8A is a diagram illustrating the behavior of a detection signal and FIG. 8B is a diagram illustrating the behavior of a projected image, when fluctuation of the microparticle in the flowing direction is not restricted. FIG. 9A is a diagram illustrating the behavior of a detection signal and FIG. 9B is a diagram illustrating the behavior of a projected image, when the fluctuation of the microparticle in the flowing direction is restricted.

Normally, it is ideal for signals in respective light receiving surfaces a, b, c, and d of the particle position detector 7 to be superposed on each other, but as illustrated in FIGS. 8A and 8B, when fluctuation of the microparticle 10 in the flowing direction x is not restricted, the signal values of respective light receiving surfaces a, b, c, and d are deviated from each other. Whereas, as in the microparticle measuring apparatus 1 according to the present embodiment, when the fluctuation of the microparticle 10 in the flowing direction x is restricted, deviation between the signal values are reduced, as illustrated in FIGS. 9A and 9B.

In order to confirm the effect of restricting the fluctuation of the microparticle 10 in the flowing direction x, a laser beam having a wavelength of 488 nm is emitted as the excitation light 11 from the light source 2 to the microparticle 10 flowing in the flow channel 3, and the fluorescence 12 and the scattered light 13 emitted from the microparticle 10 are detected. Specifically, light emitted from the microparticle 10 is collected by the objective lens, and is diffracted using the spectral filter 4 into the fluorescence 12 and the scattered light 13 according to the wavelength.

The fluorescence 12 is diffracted into fluorescence 14 using a prism as the spectral element 8, the fluorescence 14 having been diffracted by the prism according to the wavelength is projected on a 32-channel light receiving element array (fluorescence detector 9), and detected. Whereas, the scattered light 13 is diffracted by the polarization element 5. The P-polarized light 13p is detected by the scattered light intensity detector 6, and the S-polarized light 13s is projected on the quadrant photodiode (particle position detector 7).

Figure 10A:
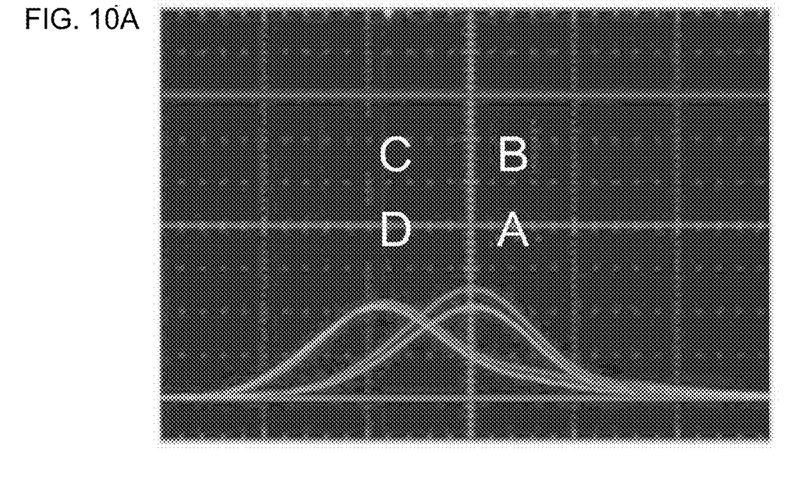
FIG. 10A is a photograph illustrating measured values of detection signals, when the fluctuation of the microparticle in the flowing direction is not restricted.
Figure 10B:
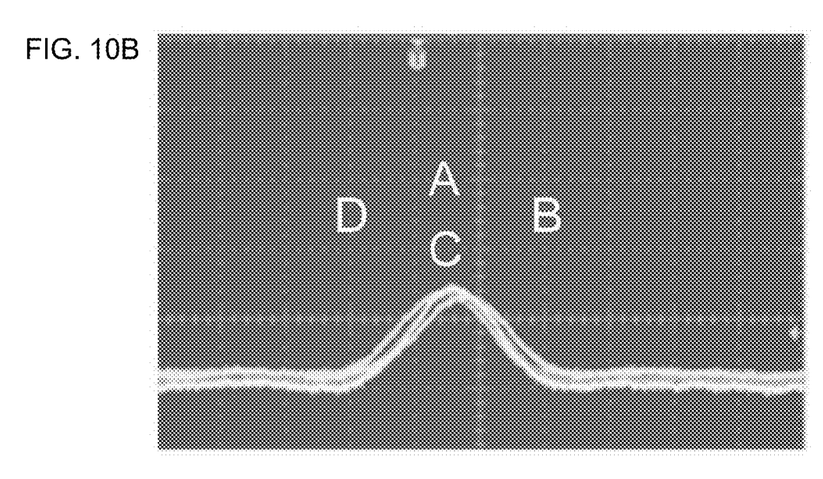
FIG. 10B is a photograph illustrating measured values of the detection signals, when the fluctuation of the microparticle in the flowing direction is restricted.

FIG. 10A is a photograph illustrating measured values of detection signals, when the fluctuation of the microparticle in the flowing direction is not restricted, and FIG. 10B is a photograph illustrating measured values of the detection signals, when the fluctuation of the microparticle in the flowing direction is restricted. As illustrated in FIGS. 10A and 10B, it was confirmed that restricted fluctuation reduces deviation between the signal values due to fluctuation of the projected image caused by misalignment of the microparticle 10 in the flowing direction x.

As described above, the microparticle measuring apparatus 1 according to the present embodiment is configured to optically restrict the fluctuation of the microparticle 10 in the flowing direction x, and therefore, the detection signal of the flowing position of the microparticle is prevented from being superposed with an unnecessary error signal. Accordingly, noise is reduced when various light detection values are corrected based on the positional information of the microparticle, so that the intensities of the fluorescence and the scattered light can be improved in CV value or accuracy in fluorescence spectrum shape. For example, by trimming processing for narrowing the analysis to the microparticles 10 flowing through a certain positional range in the laminar flow 30, variation in measured values is reduced, and dispersion or the CV value can be improved.

Further, since the microparticle measuring apparatus 1 according to the present embodiment is provided with the optical system for positional detection, in addition to the one for detection of the fluorescence 12 and the scattered light 13, a pinhole for limiting view can be eliminated, and the range of view to be projected on the light receiving surface of the particle position detector 7 can be increased. Therefore, the linearity of the detection signal is improved. Further, light scattered in the particle is transmitted while being inclined with respect to the optical axis, which significantly influences the particle having a large diameter. However, the microparticle measuring apparatus 1 according to the present embodiment is configured to capture a signal, including the scattered light transmitted while being inclined with respect to the optical axis, and thus, the dynamic range can be also increased.

The microparticle measuring apparatus 1 according to the present embodiment is configured to diffract the scattered light 13 by the polarization element 5, but the present disclosure is not limited to this configuration, and the light splitting element configured to divide the scattered light 13 into two components is preferably provided in front of the scattered light intensity detector 6 and the particle position detector 7. The light splitting element can employ a power splitting element without a polarization separation property, in addition to the above-mentioned polarization element 5. In this configuration, a ratio of light input to the scattered light intensity detector 6 to light input to the particle position detector 7 is preferably approximately 9:1.

Further, the arrangement of the microchip 20 and each optical component of the position detecting optical system is also not limited to the arrangement illustrated in FIG. 3, and, for example, the orientation of the mirror 25 can be changed to arrange the astigmatic element 22 and the particle position detector 7 on the z-axis. In this configuration, the setting angles of the astigmatic element 22 and the particle position detector 7 are preferably adjusted according to signal behavior.

2. Modification of First Embodiment

Figure 11:
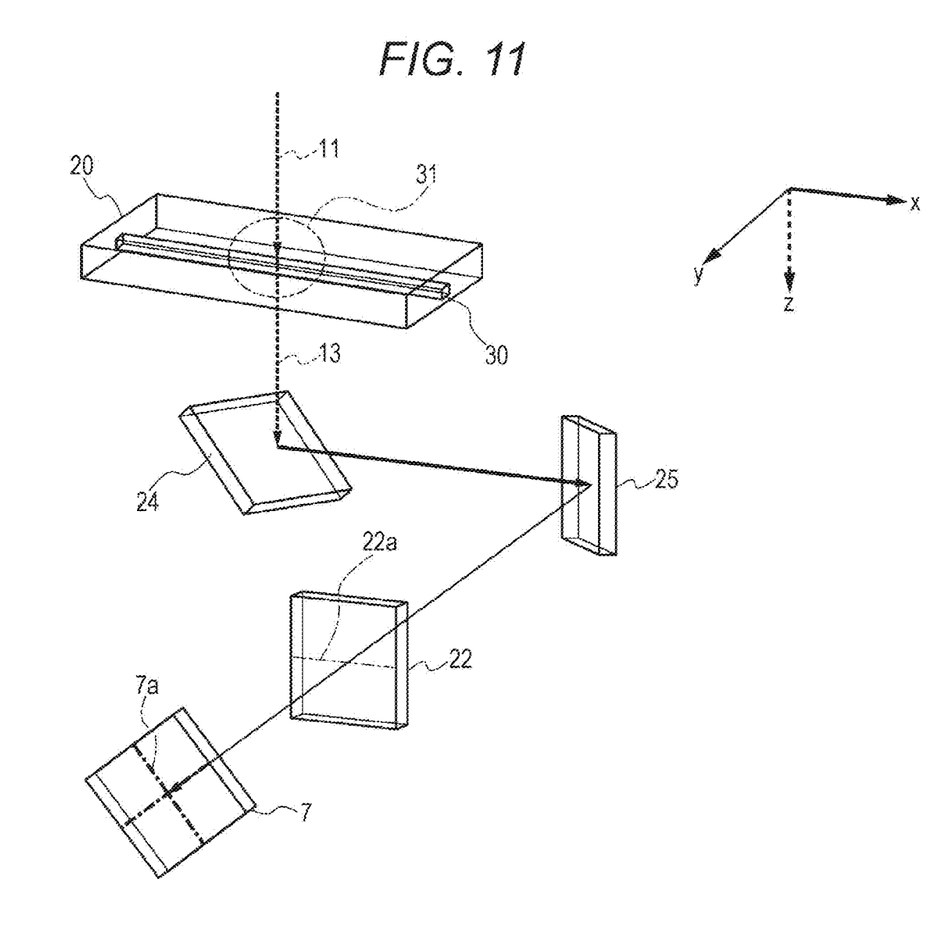
FIG. 11 is a schematic diagram illustrating arrangement of each optical component of a position detecting optical system in a microparticle measuring apparatus according to a modification of the first embodiment of the present disclosure.

The microparticle measuring apparatus 1 illustrated in FIG. 3 has a configuration in which the astigmatic element 22 is arranged so that the generatrix 22a is perpendicular to the flowing direction x of the microparticle 10, but the present disclosure is not limited to this configuration, and the generatrix 22a may be arranged to be parallel to the flowing direction x of the microparticle 10. FIG. 11 is a schematic diagram illustrating arrangement of each optical component of the position detecting optical system in the microparticle measuring apparatus according to a modification of the first embodiment of the present disclosure.

As illustrated in FIG. 11, in the microparticle measuring apparatus according to the present modification, the astigmatic element 22 has a generatrix 22a arranged on the y-axis to be substantially parallel to the flowing direction x of the microparticle 10. Specifically, the astigmatic element 22 is arranged on a plane perpendicular to the y-axis to have an angle of 0° to 5° between the generatrix 22a and a line extending in the x-axis direction.

Further, the particle position detector 7 is also arranged on the y-axis. For example, a quadrant detector has a dividing line 7a arranged so as to be positioned substantially at ±45° to the flowing direction x of the microparticle 10. Specifically, the particle position detector 7 is preferably arranged on a plane perpendicular to the y-axis to have an angle of 40° to 50° between the dividing line 7a and a line extending in the x-axis direction and the z-axis direction. Also in this configuration, an angle between the generatrix 22a of the astigmatic element 22 and the dividing line 7a of the particle position detector 7 is substantially ±45°.

Also in the present modification, as similar to the above-mentioned microparticle measuring apparatus according to the first embodiment, since the influence of positional fluctuation of the microparticle in the flowing direction can be restricted, the position of the microparticle flowing through the flow channel can be detected highly accurately, as compared with a conventional one. It is noted that the other configurations and effects of the present modification are similar to those of the first embodiment having been described above.

Further, the present disclosure can also employ the following configuration.

(1) A microparticle measuring apparatus including:

a light irradiation unit configured to irradiate a microparticle flowing through a flow channel with light; and a scattered light detection unit configured to detect scattered light from the microparticle, the scattered light detection unit at least including:

an objective lens configured to collect light emitted from the microparticle;

a light splitting element configured to divide the scattered light from the light having been collected by the objective lens, into first scattered light and second scattered light;

a first scattered light detector configured to receive the first scattered light; and an astigmatic element disposed between the light splitting element and the first scattered light detector, the astigmatic element configured to make the first scattered light astigmatic, wherein a relationship between a length L from a rear principal point of the objective lens to a front principal point of the astigmatic element, and a focal length f of the astigmatic element satisfies the following formula (I).

$$1.5f \leq L \leq 2.5f \qquad (I)$$

(2) The microparticle measuring apparatus according to (1), wherein the light splitting element is a polarization element configured to diffracting the scattered light into an S-polarized light component and a P-polarized light component, and the first scattered light is the S-polarized light component.

(3) The microparticle measuring apparatus according to (1) or (2), wherein the astigmatic element is a cylindrical lens.

(4) The microparticle measuring apparatus according to any of (1) to (3), wherein when a light input direction to the microparticle is defined as the z-direction, a flowing direction of the microparticle is defined as the x-direction, and a direction perpendicular to the z- and x-directions is defined as the y-direction, the astigmatic element is disposed on a plane perpendicular to a y-direction to have an angle 0° to 5° between a generatrix of the astigmatic element and a line extending in an x-direction or a line extending in a z-direction.

(5) The microparticle measuring apparatus according to any of (1) to (4), wherein the first scattered light detector is a detector having a light receiving surface divided into a plurality of areas.

(6) The microparticle measuring apparatus according to any of (1) to (5), wherein the first scattered light detector is a quadrant photodiode.

(7) The microparticle measuring apparatus according to any of (1) to (6), wherein when the light input direction to the microparticle is defined as the z-direction, the flowing direction of the microparticle is defined as the x-direction, and the direction perpendicular to the z- and x-directions is defined as the y-direction, the first scattered light detector is disposed on a plane perpendicular to the y-direction to have an angle of 40° to 50° between a dividing line of the first scattered light detector and a line extending in the x-direction or a line extending in the z-direction.

(8) The microparticle measuring apparatus according to any of (1) to (7), wherein a flowing position of the microparticle is detected based on the change in light receiving position of the first scattered light.

(9) The microparticle measuring apparatus according to any of (1) to (8), wherein
the light receiving surface of the first scattered light detector is divided into a lattice shape to have a first area, a second area, a third area, and a fourth area, and
the first scattered light detector acquires the positional information of the microparticle based on a difference (A-C) between a detection value A of the first area and a detection value C of the third area not adjacent to the first area.

(10) The microparticle measuring apparatus according to any of (1) to (8), wherein
the light receiving surface of the first scattered light detector is divided into a lattice shape to have a first area, a second area, a third area, and a fourth area, and
the first scattered light detector acquires the positional information of the microparticle based on a difference ((A+C)−(B+D)) between the sum (A+C) of the detection value A of the first area and the detection value C of the third area not adjacent to the first area, and the sum (B+D) of a detection value B of the second area adjacent to the first area and a detection value D of the fourth area not adjacent to the second area.

(11) The microparticle measuring apparatus according to any of (1) to (10), wherein the light irradiation unit irradiates the microparticle flowing through an analysis chip including a microchannel, with light.

REFERENCE SIGNS LIST

1 Microparticle measuring apparatus
2 Light source
3 Flow channel
4 Spectral filter
5 Polarization element
6 Scattered light intensity detector
7 Particle position detector
7a Dividing line
8 Spectral element
9 Fluorescence detector
9a to 9z Light receiving element
10 Microparticle
11 Excitation light
12, 14 Fluorescence
13 Scattered light
13s S-polarized light
13p P-polarized light
20 Microchip
21 Objective lens
22 Astigmatic element
22a Generatrix
23 Condensing lens
24, 25 Mirror
30 Laminar flow
31 Excitation light irradiation unit

The invention claimed is:
1. An apparatus, comprising:
a light source configured to irradiate a microparticle with first light;
an objective lens configured to collect second light emitted from the microparticle;
a scattered light detector configured to receive scattered third light from the second light collected by the objective lens; and
an astigmatic element between the objective lens and the scattered light detector,
wherein the astigmatic element is configured to make the scattered third light astigmatic,
wherein a relationship between a length L from a rear principal point of the objective lens to a front principal point of the astigmatic element and a focal length f of the astigmatic element satisfies the following formula (I)

$$1.5f \leq L \leq 2.5f \quad (I).$$

2. The apparatus according to claim 1, further comprising a light splitting element configured to divide the scattered third light from the second light collected by the objective lens into a fourth scattered light and a fifth scattered light,
wherein the fourth scattered light is received by the scattered light detector.

3. The apparatus according to claim 2, wherein the light splitting element is a polarization element,
wherein the polarization element is configured to diffract the scattered third light into an S-polarized light component and a P-polarized light component,
wherein the fourth scattered light is the S-polarized light component.

4. The apparatus according to claim 1, wherein the astigmatic element is a cylindrical lens.

5. The apparatus according to claim 4, wherein the astigmatic element is positioned on a plane perpendicular to a v-direction based on:
a light input direction to the microparticle defined as a z-direction,
a direction of flow of the microparticle defined as a x-direction, and
a direction perpendicular to the z-direction and the x-direction defined as the y-direction,
wherein the astigmatic element is further configured to have an angle of 0° to 5° between a generatrix of the astigmatic element and a first line that extends in the x-direction or a second line that extends in the z-direction.

6. The apparatus according to claim 1, wherein the scattered light detector comprises a light receiving surface divided into a plurality of areas.

7. The apparatus according to claim 6, wherein the scattered light detector is a quadrant photodiode.

8. The apparatus according to claim 7, wherein the scattered light detector is further configured on a plane perpendicular to a y-direction based on:
a light input direction to the microparticle defined as a z-direction,
a direction of flow of the microparticle defined as a x-direction, and
a direction perpendicular to the z-direction and the x-direction defined as the y-direction,
wherein the scattered light detector is further configured to have an angle of 40° to 50° between a first line that divides the scattered light detector and a second line that extends in the x-direction or a third line that extends in the z-direction.

9. The apparatus according to claim 1, wherein a first position of flow of the microparticle is detected based on a change in second position of reception of the scattered third light.

10. The apparatus according to claim 9, wherein
a light receiving surface of the scattered light detector is divided into a lattice shape to have a first area, a second area, a third area, and a fourth area, and
the scattered light detector is further configured to acquire positional information of the microparticle based on a difference (A-C) between a detection value A of the first area and a detection value C of the third area that is separately positioned from the first area.

11. The apparatus according to claim 9, wherein
a light receiving surface of the scattered light detector is divided into a lattice shape to have a first area, a second area, a third area, and a fourth area, and
the scattered light detector is further configured to acquire positional information of the microparticle based on a difference ((A+C)−(B+D)) between a sum (A+C) of a detection value A of the first area and a detection value C of the third area that is separately positioned from the first area, and a sum (B+D) of a detection value B of the second area adjacent to the first area and a detection value D of the fourth area that is separately positioned from the second area.

12. A flow cytometer, comprising:
a light source configured to irradiate a microparticle with first light, wherein the microparticle flows through a flow channel;
an objective lens configured to collect second light emitted from the microparticle;
a scattered light detector configured to receive third scattered light from the second light collected by the objective lens, wherein the third scattered light is scattered by the microparticle; and
an astigmatic element between the objective lens and the scattered light detector,
wherein the astigmatic element is configured to make the third scattered light astigmatic,
wherein a relationship between a length L from a rear principal point of the objective lens to a front principal point of the astigmatic element and a focal length f of the astigmatic element satisfies the following formula (I)

$$1.5f \leq L \leq 2.5f \qquad (I).$$

13. The flow cytometer according to claim 12, wherein the light source is further configured to irradiate the microparticle with the first light, wherein the microparticle flows through an analysis chip,
wherein the analysis chip includes the flow channel.

14. The flow cytometer according to claim 12, further comprising a light splitting element configured to divide the third scattered light from the second light that is collected by the objective lens into a fourth scattered light and a fifth scattered light, wherein the fifth scattered light is received by the scattered light detector.

15. The flow cytometer according to claim 14, wherein the light splitting element is a polarization element, wherein the polarization element is configured to diffract the third scattered light into an S-polarized light component and a P-polarized light component, wherein the fourth scattered light is the S-polarized light component.

16. The flow cytometer according to claim 12, wherein the astigmatic element is a cylindrical lens.

17. The flow cytometer according to claim 12, wherein the scattered light detector comprises a light receiving surface divided into a plurality of areas.

18. The flow cytometer according to claim 17, wherein the scattered light detector is a quadrant photodiode.

19. The flow cytometer according to claim 12, wherein a first position of flow of the microparticle is detected based on a change in second position of reception of the third scattered light.

20. The flow cytometer according to claim 19, wherein
a light receiving surface of the scattered light detector is divided into a lattice shape to have a first area, a second area, a third area, and a fourth area, and
the scattered light detector is further configured to acquire positional information of the microparticle based on a difference (A-C) between a detection value A of the first area and a detection value C of the third area that is separately positioned from the first area.

\* \* \* \* \*